(12) United States Patent
Kao

(10) Patent No.: US 10,293,070 B2
(45) Date of Patent: May 21, 2019

(54) WASTE GAS SCRUBBING TOWER

(71) Applicant: Ying-Hao Kao, Kaohsiung (TW)

(72) Inventor: Ying-Hao Kao, Kaohsiung (TW)

( * ) Notice: Subject to any disclaimer, the term of this patent is extended or adjusted under 35 U.S.C. 154(b) by 232 days.

(21) Appl. No.: 15/480,376

(22) Filed: Apr. 6, 2017

(65) Prior Publication Data

US 2017/0304480 A1    Oct. 26, 2017

(30) Foreign Application Priority Data

Apr. 22, 2016    (TW) .............................. 105112585 A

(51) Int. Cl.
| | | |
|---|---|---|
| *A61L 9/14* | (2006.01) | |
| *B01D 46/00* | (2006.01) | |
| *B01D 47/06* | (2006.01) | |
| *B01D 53/14* | (2006.01) | |
| *B01D 53/78* | (2006.01) | |
| *B01D 53/72* | (2006.01) | |
| *B01D 47/14* | (2006.01) | |

(52) U.S. Cl.
CPC .......... *A61L 9/145* (2013.01); *B01D 46/0023* (2013.01); *B01D 46/0038* (2013.01); *B01D 47/06* (2013.01); *B01D 47/14* (2013.01); *B01D 53/1493* (2013.01); *B01D 53/72* (2013.01); *B01D 53/78* (2013.01); *A61L 2209/14* (2013.01); *A61L 2209/22* (2013.01); *B01D 2221/02* (2013.01); *B01D 2247/04* (2013.01); *B01D 2252/103* (2013.01); *B01D 2257/90* (2013.01); *B01D 2258/0275* (2013.01)

(58) Field of Classification Search
CPC .. A61L 2209/14; A61L 2209/22; A61L 9/145; B01D 2221/02; B01D 2247/04; B01D 2252/103; B01D 2257/90; B01D 2258/0275; B01D 46/0023; B01D 46/0038; B01D 47/06; B01D 47/14; B01D 53/1493; B01D 53/72; B01D 53/78
See application file for complete search history.

(56) References Cited

U.S. PATENT DOCUMENTS

2010/0229725 A1* 9/2010 Farsad ............... B01D 53/1456
                                                           96/74

* cited by examiner

Primary Examiner — Cabrena Holecek
(74) Attorney, Agent, or Firm — Leong C. Lei

(57) ABSTRACT

A waste gas scrubbing tower includes a tower body unit, a filtration unit arranged in the tower body unit, a washing unit that introduces water from an external supply into the tower body unit. The tower body unit includes division boards that define a plurality of channels through which waste gas flows, the tower body unit including a waste gas inlet opening and a waste gas outlet opening. The filtration unit includes a plurality of filter members, which are arranged in the channels. The washing unit is operable to generate water mist curtains in the channels to wash the waste gas so that the waste gas that enters the waste gas scrubbing tower is subjected to multiple times of washing and filtration and purification.

11 Claims, 5 Drawing Sheets

WASTE GAS SCRUBBING TOWER

(A) TECHNICAL FIELD OF THE INVENTION

The present invention relates generally to a waste gas scrubbing tower, and more particularly to a waste gas scrubbing tower that improves a deodorization effect of the waste gas scrubbing tower.

(B) DESCRIPTION OF THE PRIOR ART

Industry, animal husbandry, and food service business often generate waste gases that make people uncomfortable. Such businesses that generate waste gases are often under protest by local residents, and various solutions have been proposed in such businesses to dissolve the issue of odors of the waste gases.

Taking food service business as an example, certain food materials used in the food service business, when cooked, may generate high concentration odor smell, such as garlic, chili, and certain fermented foodstuffs. The high concentration odor smell generated in cooking such food materials often causes troubles to people. Waste gas scrubbing towers are commonly used in the food service business to alleviate or eliminate the troublesome odor smell in order to reduce the annoying issues.

As shown in FIG. 1, a conventional waste gas scrubbing tower 1 comprises a tower body 11 and a washing device 12 mounted in the tower body 11. The tower body 11 comprises a waste gas inlet opening 111, a waste gas outlet opening 112, and a drainage opening 113. Waste gas moves through the waste gas inlet opening 111 into the tower body 11. The washing device 12 comprises sprinklers 121 and the sprinklers 121 sprays water supplied from the outside to conduct a washing operation on the waste gas moving into the tower body 11. The waste gas so washed out and cleaned is discharged out of the tower body 11 through the waste gas outlet opening 112. In this way, minute particles contained in the waste gas are reduced and the smell of the waste gas is lowered down. The minute particles so washed out and left in the tower body 11 and the water so used are then drained out of the tower body 11 through the drainage opening 113.

The known waste gas scrubbing tower, although effective in lowering down the odor smell of the waste gas through the above-described structure, is not good enough to remove the odor smell of the waste gas to such an extent as to make people not feeling annoying. Thus, it is a challenge of the waste gas scrubbing tower manufacturers to provide a waste gas scrubbing tower that effectively overcomes the annoying odor smell of cooking waste gases.

SUMMARY OF THE INVENTION

The primary objective of the present invention is to provide a waste gas scrubbing tower for the purposes of overcoming the drawback of the conventional waste gas scrubbing towers having a poor effect of deodorization.

To achieve the objective, a technical solution as claimed in claim 1 of the present invention provides a waste gas scrubbing tower. The waste gas scrubbing tower comprises a tower body unit, a filtration unit arranged in the tower body unit, a washing unit that introduces water from an external supply into the tower body unit. The tower body unit comprises division boards that define a plurality of channels through which waste gas flows, the tower body unit comprising a waste gas inlet opening and a waste gas outlet opening. The filtration unit comprises a plurality of filter members, which are arranged in the channels. The washing unit is operable to generate water mist curtains in the channels to wash the waste gas so that the waste gas that enters the waste gas scrubbing tower is subjected to multiple times of washing and filtration and purification.

The efficacy that the technical solution claimed in claim 1 of the present invention may achieves is that by arranging a plurality of channels through which waste gas may flow inside a tower body unit and arranging filter members of a plurality of filtration unit in the channels, with washing water mist curtains generated by a washing unit inside each of the channels, waste gas that enters the waste gas scrubbing tower may be subjected to multiple times of washing by water mist curtains and multiple times of filtration and purification to have odor smell and minute particles contained in the waste gas effectively removed so as to enhance utilization performance of the waste gas scrubbing tower.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
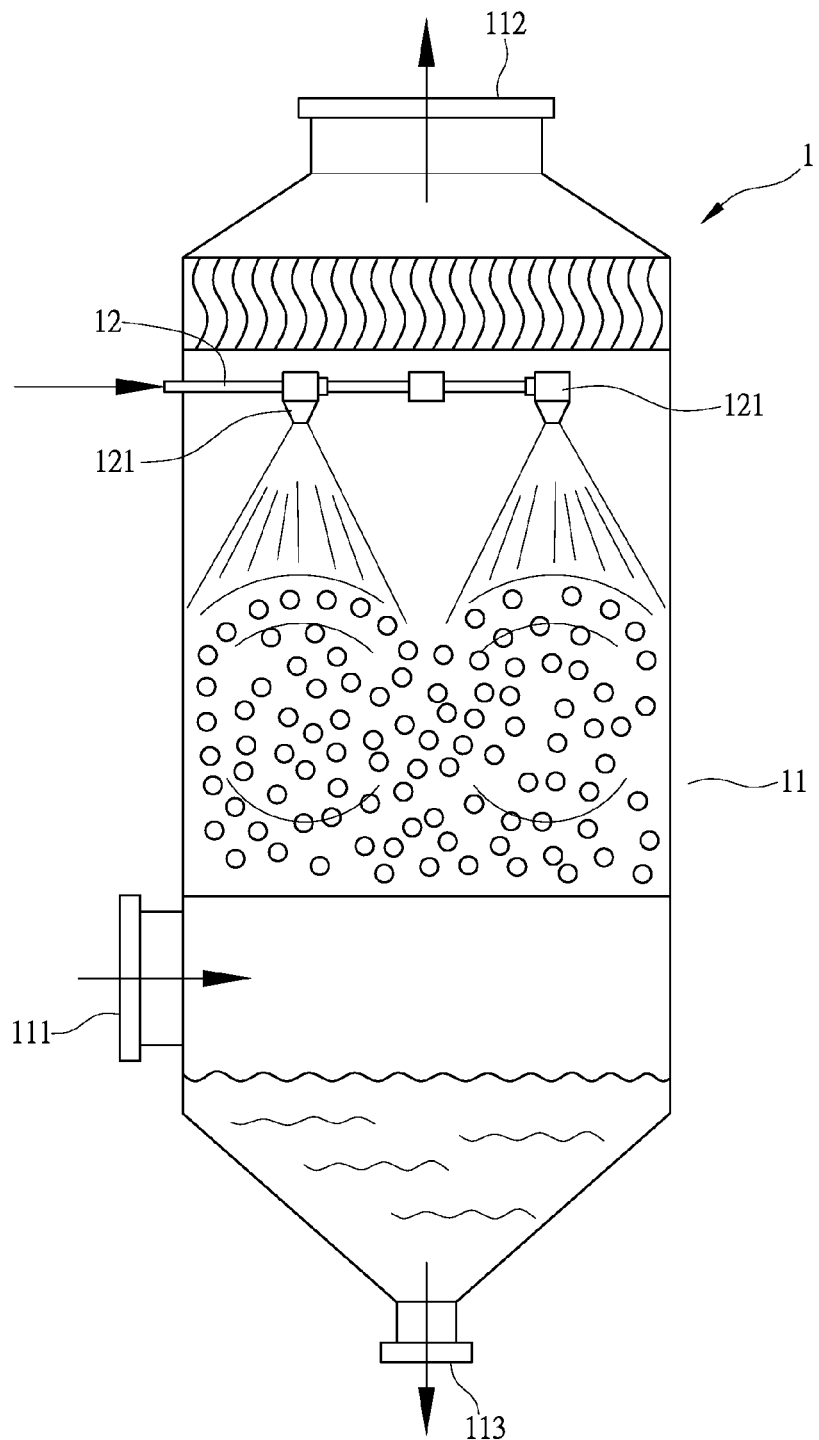
FIG. 1 is a schematic view showing a conventional waste gas scrubbing tower.
Figure 2:
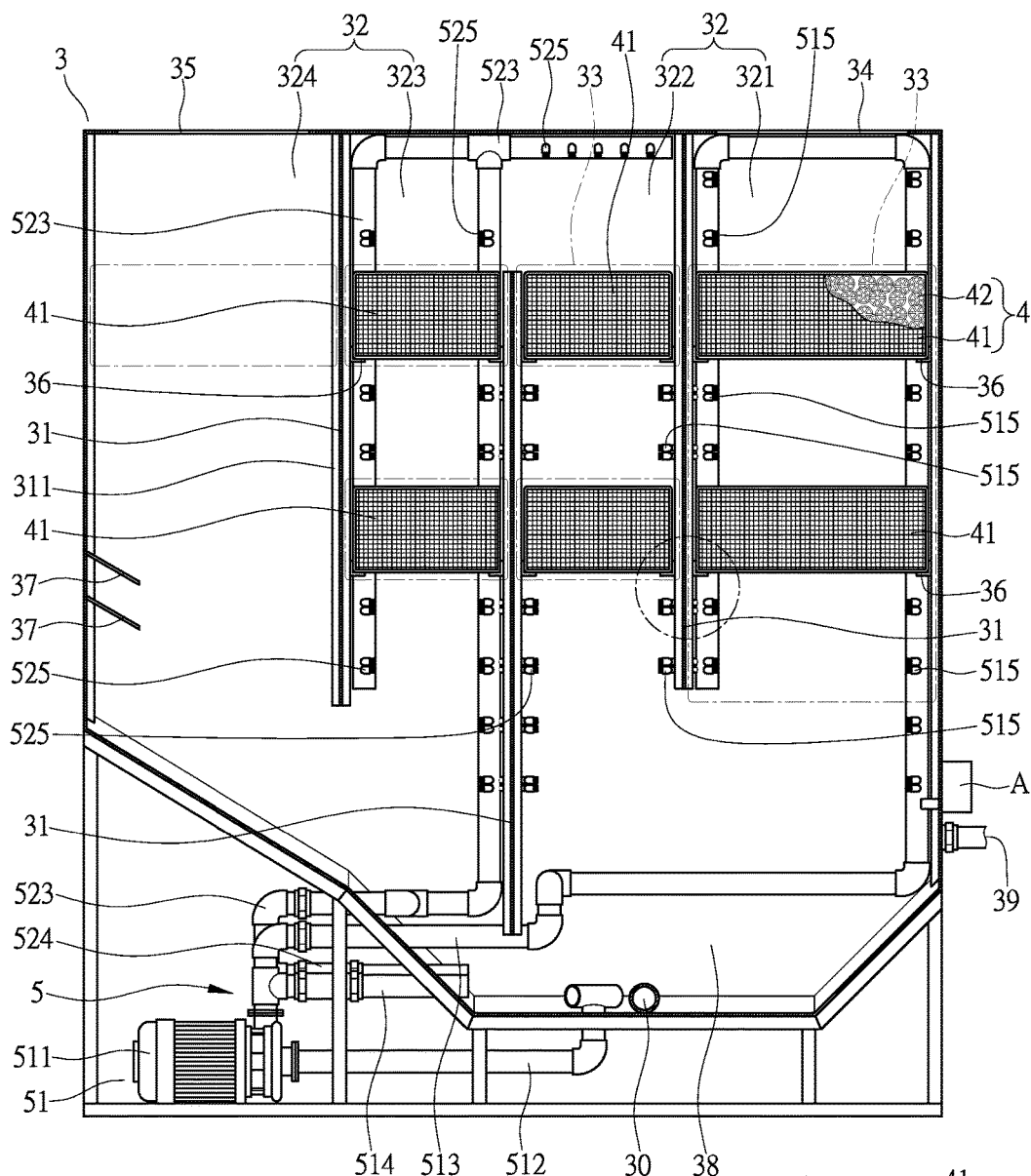
FIG. 2 is a schematic view illustrating a waste gas scrubbing tower according to the present invention.
Figure 2A:
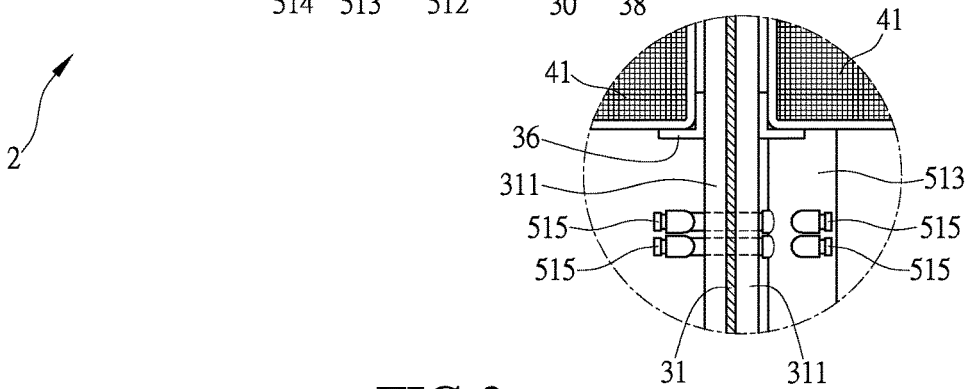
FIG. 2A is an enlarged view of a circled portion of FIG. 2.
Figure 3:
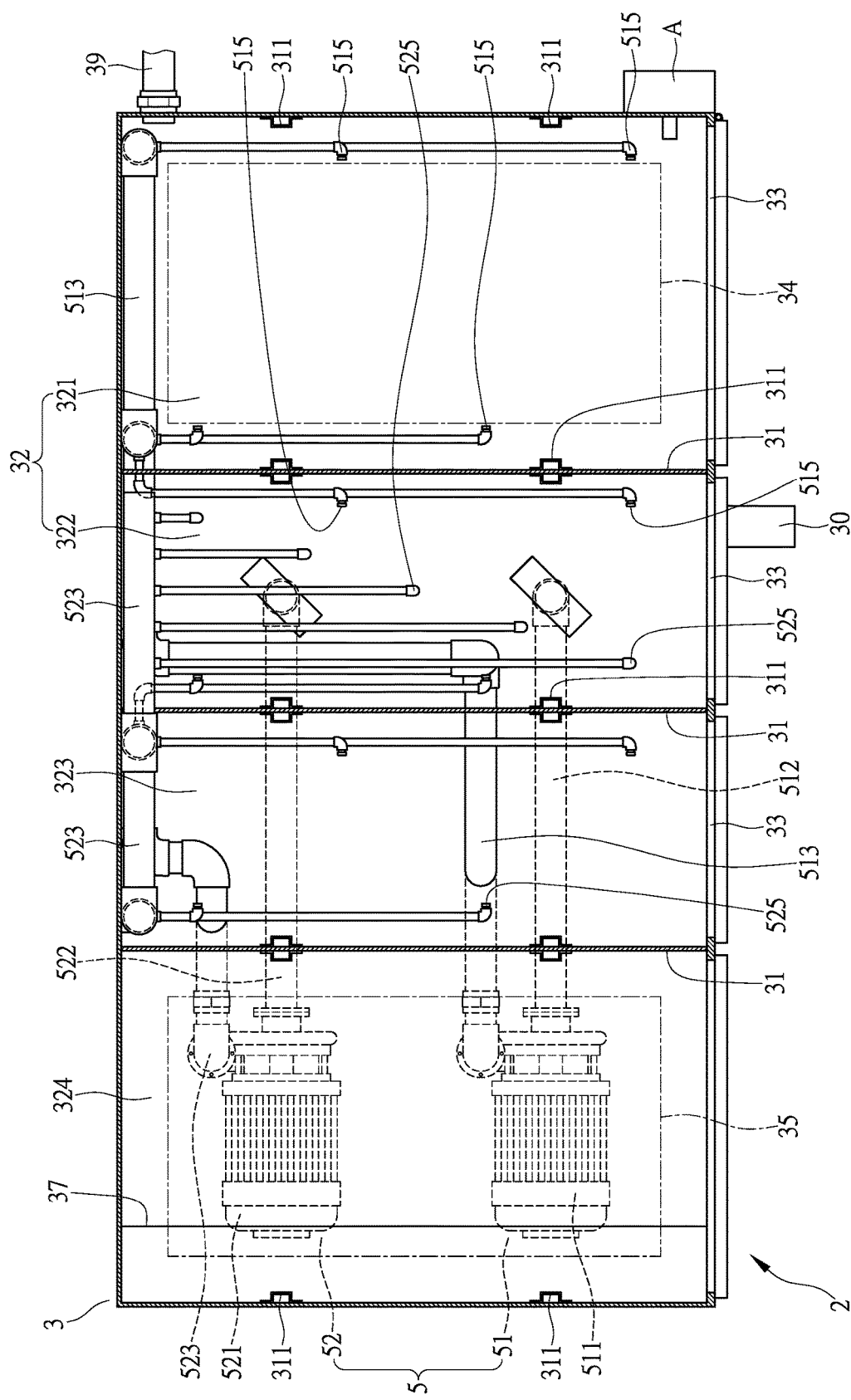
FIG. 3 is a top plan view of the waste gas scrubbing tower according to the present invention.

Firstly, referring to FIGS. 2 and 3, the present invention provides a waste gas scrubbing tower. The waste gas scrubbing tower, generally designated at 2, comprises a tower body unit 3, a filtration unit 4 arranged in the tower body unit 3, and a washing unit 5 that introduces water from an external supply into the tower body unit 3.

As shown in FIGS. 2 and 3, the tower body unit 3 comprises a plurality of division boards 31 arranged therein to define a plurality of channels 32 that are in communication with each other. In the instant embodiment, four channels 32 are taken as an example of the present invention for illustration and are respectively referred, in sequence, to as a first channel 321, a second channel 322, a third channel 323, and a fourth channel 324. The channels 32 are provided, at one side thereof, with a plurality of filter mounting openings 33. The filter mounting openings 33 are provided for installation, as well as replacement, of filter members 41 of the filtration unit 4 inside the tower body unit 3. Among the channels 32, the first channel 321 is formed, in an upper end thereof, with a waste gas inlet opening 34, and a lower end of the first channel 321 is set in communication with the second channel 322; the second channel 322 has an upper end that is set in communication with the third channel 323; the third channel 323 has a lower end that is set in communication with the fourth channel 324; and the fourth channel 324 is formed, in an upper end thereof, with a waste gas outlet opening 35; and further, the first channel 321, the second channel 322, and the third channel 323 are provided with a plurality of filter member mounting sections 36 for mounting the filtration unit 4. The filter member mounting sections 36 are formed of reinforcement ribs formed on and projecting from the division boards 31. The fourth channel 324 is provided with water blocking plates 37 that project, in an inclined condition, in a direction toward the third channel 323. The water blocking plates 37 are provided in multiplicity. The tower body unit 3 has a bottom portion that forms a water accumulation section 38 in a converging form. The water accumulation section 38 is provided, on an upper side thereof, with an overflow opening 39 and a water level controller A. The overflow opening 39 extends from the water accumulation section 38 to the outside of the tower body unit 3. The water level controller A controls a water level of the water accumulation section 38 so that when the water level of the water accumulation section 38 is lower than a predetermined height, the water level controller A automatically conducts water into the water accumulation section 38. The tower body unit 3 is provided, on a bottom of the water accumulation section 38, with a waste water drainage opening 30. The waste water drainage opening 30 drains waste water contained in the water accumulation section 38 to the outside of the tower body unit 3.

As shown in FIGS. 2 and 3, the filtration unit 4 comprises a plurality of filter members 41. The filter members 41 comprise, arranged therein, a plurality of filter elements 42. The filtration unit 4 is mounted on the filter member mounting sections 36 of the tower body unit 3. More specifically, the filtration unit 4 is mounted in the first channel 321, the second channel 322, and the third channel 323 of the channels 32 and is arranged in the first channel 321, the second channel 322, and the third channel 323 in a manner of being separated at upper and lower sides.

As shown in FIGS. 2 and 3, the washing unit 5 comprises a first washing assembly 51 and a second washing assembly 52. The first washing assembly 51 comprises a first pump assembly 511, a first water drawing pipe 512 connected to the first pump assembly 511, a first water conveyance pipe assembly 513 connected to the first pump assembly 511, a first pressure regulation pipe 514 connected to the first pump assembly 511, and a plurality of first spraying head assemblies 515 connected to the first water conveyance pipe assembly 513. The second washing assembly 52 comprises a second pump assembly 521, a second water drawing pipe 522 connected to the second pump assembly 521, a second water conveyance pipe assembly 523 connected to the second pump assembly 521, a second pressure regulation pipe 524 connected to the second pump assembly 521, and a plurality of second spraying head assemblies 525 connected to the second water conveyance pipe assembly 523.

As shown in FIGS. 2 and 3, the first washing assembly 51 uses the first pump assembly 511 to draw water, through the first water drawing pipe 512, from a lower portion of the water accumulation section 38 of the tower body unit 3, where water is considered clean, in a relative sense, such that the water so drawn in is subjected to pressure regulation by means of the first pressure regulation pipe 514, and is then conveyed through the first water conveyance pipe assembly 513 to the first channel 321 of the tower body unit 3, with a portion thereof being supplied to the second channel 322. The first spraying head assemblies 515 that are connected to the first water conveyance pipe assembly 513 are arranged, in a manner of being opposite to each other and being position-shifted from each other in the vertical direction, in the first channel 321 so that when the first pump assembly 511 supplies water from the water accumulation section 38 to the first spraying head assemblies 515, the first spraying head assemblies 515 spray water jets, in mist form, which intersect and overlap each other to form a water mist curtain for washing waste gas moving into the first channel 321.

As shown in FIGS. 2 and 3, the second washing assembly 52 uses the second pump assembly 521 to draw water, through the second water drawing pipe 522, from a lower portion of the water accumulation section 38 of the tower body unit 3, where water is considered clean, in a relative sense, such that the water so drawn in is subjected to pressure regulation by means of the second pressure regulation pipe 524, and is then conveyed through the second water conveyance pipe assembly 523 into the second channel 322 and the third channel 323 of the tower body unit 3. The second spraying head assemblies 525 that are connected to the second water conveyance pipe assembly 523 are arranged, in a manner of being opposite to each other and being position-shifted from each other in the vertical direction, in the second channel 322 and the third channel 323, some being arranged in the second channel 322 in a manner of being position-shifted with respect to the first spraying head assemblies 515 of the first washing assembly 51 in the vertical direction. In addition, the second channel 322 is additionally provided, on a top thereof, with the second spraying head assemblies 525, namely the second channel 322 comprises water mist spraying from the top side to the lower side, so that when the second pump assembly 521 supplies water from the water accumulation section 38 to the second spraying head assemblies 525, the second spraying head assemblies 525 spray water jets, in mist form, which intersect and overlap each other to form a water mist curtain for washing waste gas moving into the second channel 322 and the third channel 323.

Figure 4:
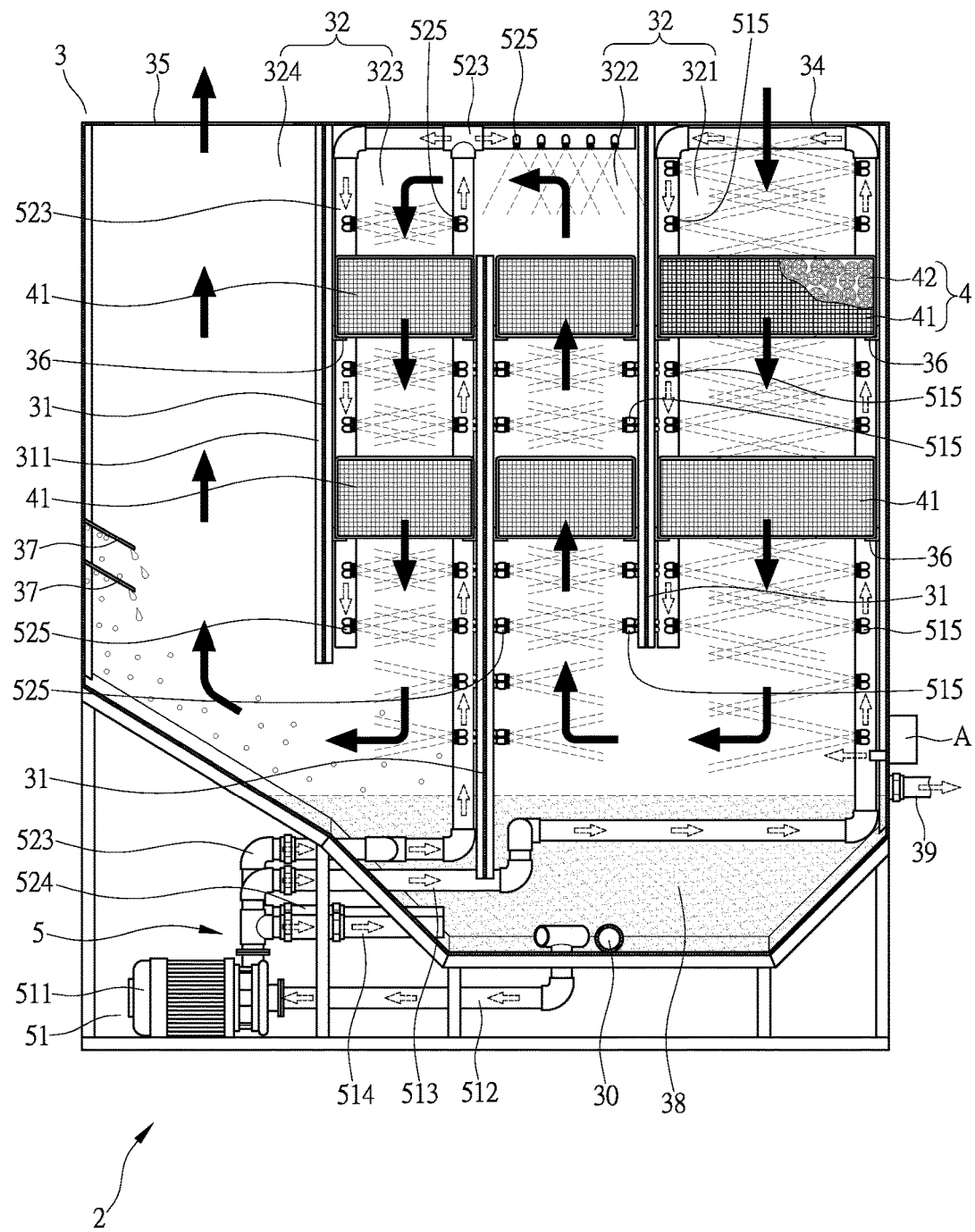
FIG. 4 is a schematic view illustrating waste gas flows and a washing operation conducted inside the waste gas scrubbing tower according to the present invention.
Figure 5:
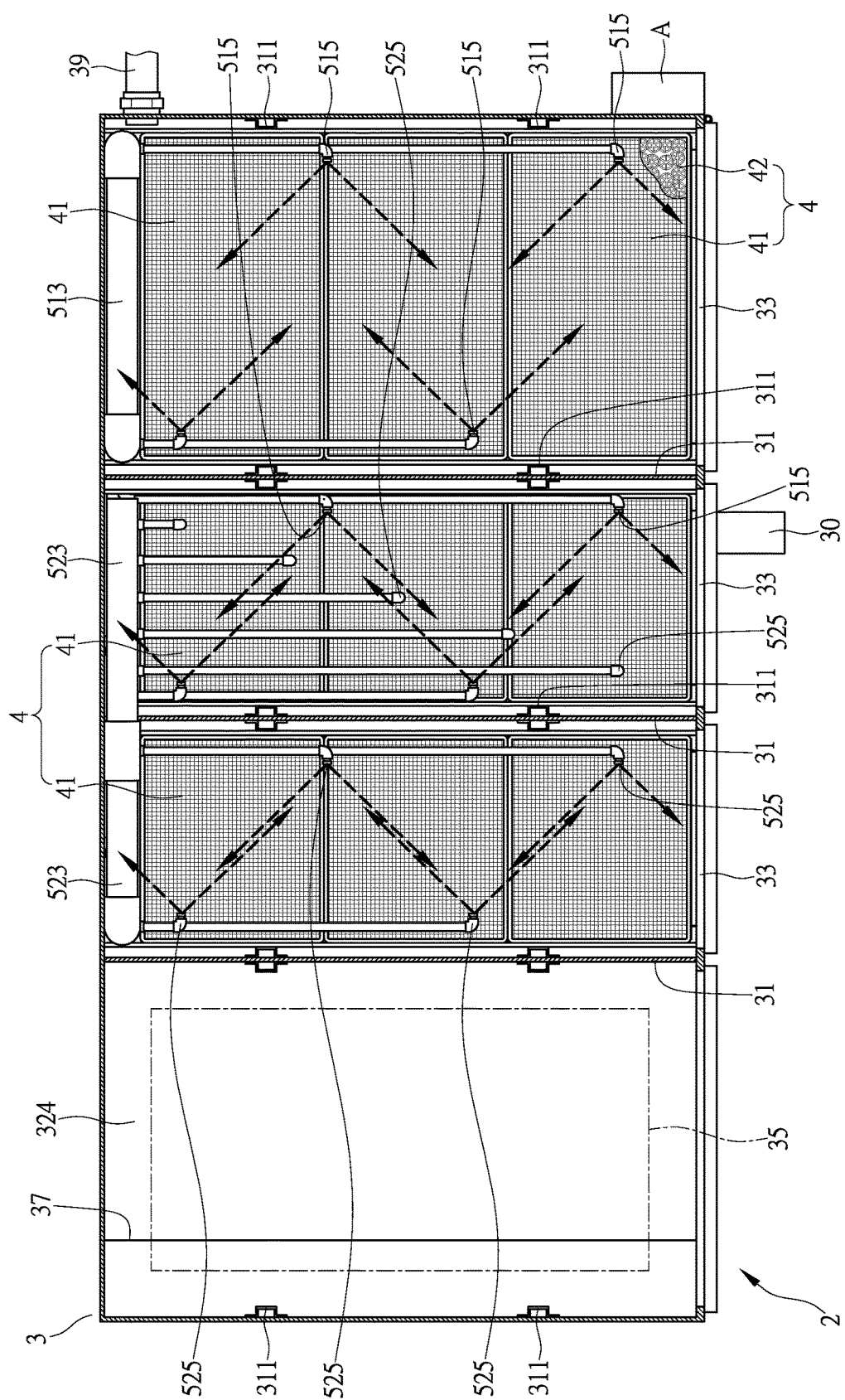
FIG. 5 is a schematic view illustrating a washing unit of the waste gas scrubbing tower spraying water mist curtains according to the present invention.

As shown in FIGS. 3, 4, and 5, to use the present invention, high concentration cooking waste gas is introduced into the first channel 321 of the tower body unit 3 through the waste gas inlet opening 34 of the tower body unit 3 and at the same time, the washing unit 5 is activated and put into operation to generate a washing water curtain in the channels 32 of the tower body unit 3. When the waste gas moves into the first channel 321, the waste gas advances in a direction from the upper side to the lower side and is subjected to washing by the water curtain inside the first channel 321 and at the same time, the filter members 41 of the filtration unit 4 mounted in the first channel 321 provide a filtration operation to remove minute particles contained in the waste gas. After the initial washing and filtration in the first channel 321, the waste gas moves from the lower end of the first channel 321 into the second channel 322, where the waste gas moves upward from the lower side to the upper side and the water mist curtain of the second channel 322 subject the waste gas to second-time washing in a manner of being directed from the upper side to the lower side and also from left side and right side and interesting each other. At the same time, the filter members 41 of the filtration unit 4 mounted in the second channel 322 provide a second-time purification operation to remove minute particles contained in the waste gas. The waste gas, after passing through the second channel 322, moves from the upper end of the second channel 322 into the third channel 323, where the waste gas moves downward from the upper side to the lower side. Once entering the third channel 323, the waste gas is subjected to a third-time washing operation by water mists curtains inside the third channel 323 spraying from left and right sides and intersecting each other. At the same time, the filter members 41 of the filtration unit 4 mounted in the third channel 323 provide a third-time purification operation to remove minute particles contained in the waste gas. Afterwards, the waste gas moves from the lower end of the third channel 323 into the fourth channel 324. When entering the fourth channel 324, the waste gas has also ready subjected to three times of washing and three times of purification by the filter members 41 of the filtration unit 4 so that no annoying odor smell may be present. Thus, the waste gas that enters the fourth channel 324 is acted upon by the water blocking plates 37 to remove water particles contained therein and then discharged to the atmosphere through the waste gas outlet opening 35 in the upper end of the fourth channel 324. Oil/grease or minute particles contained in the waste gas are partly stuck to the filter members 41 of the filtration unit 4 and partly washed away by the water mist curtain and thus floating on the water contained in the water accumulation section 38. The waste water drainage opening 30 may be opened to drain all the waste water contained in the water accumulation section 38 and replaced with clean water to set the waste gas scrubbing tower 2 of the present invention in a condition of being ready for the next operation.

The efficacy of the present invention is that by arranging a plurality of channels 32 through which waste gas may flow inside a tower body unit 3 and arranging filter members 41 of a plurality of filtration unit 4 in the channels 32, with washing water mist curtains generated by a washing unit inside each of the channels 32, waste gas that enters the waste gas scrubbing tower 2 may be subjected to multiple times of washing by water mist curtains and multiple times of filtration and purification to have odor smell and minute particles contained in the waste gas effectively removed so as to enhance utilization performance of the waste gas scrubbing tower 2. It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A waste gas scrubbing tower, comprising a tower body unit, a filtration unit arranged in the tower body unit, a washing unit that introduces water from an external supply into the tower body unit, wherein the tower body unit comprises division boards that define a plurality of channels through which waste gas flows, the tower body unit comprising a waste gas inlet opening and a waste gas outlet opening; the filtration unit comprises a plurality of filter members, which are arranged in the channels; the washing unit is operable to generate water mist curtains in the channels to wash the waste gas so that the waste gas that enters the waste gas scrubbing tower is subjected to multiple times of washing and filtration and purification, wherein the washing unit comprises a plurality of washing assemblies that each comprise a pump assembly, a water drawing pipe connected to the pump assembly, a water conveyance pipe assembly connected to the pump assembly, a pressure regulation pipe connected to the pump assembly, a plurality of spraying head assemblies connected to the water conveyance pipe assembly, the spraying head assemblies being arranged in a manner of being opposite to each other and position-shifted from each other in a vertical direction.

2. The waste gas scrubbing tower according to claim 1, wherein the tower body unit is provided, at one side thereof, with a plurality of filter mounting openings, one the plurality of channels being provided with a waste gas inlet opening in an upper end thereof, another one of the plurality of channels being provided with a waste gas outlet opening in an upper end thereof; the plurality of channels are provided with a plurality of filter member mounting sections for mounting the filter members of the filtration unit, the filter member mounting sections being formed of reinforcement ribs projecting from the division boards; the one of the channels that is provided with the waste gas outlet opening comprising water blocking plates arranged therein; and the filter members comprising a plurality of filter elements arranged therein.

3. The waste gas scrubbing tower according to claim 1, wherein the tower body unit has a bottom portion that forms a water accumulation section in a converging form, the water accumulation section being provided, on an upper side thereof, with an overflow opening and a water level controller; and the tower body unit is provided, on a bottom of the water accumulation section, with a waste water drainage opening.

4. The waste gas scrubbing tower according to claim 1, wherein the plurality of channels of the tower body unit are connected to and in communication with each other, the plurality of channels being sequentially a first channel, a second channel, a third channel, and a fourth channel; the first channel is formed, in an upper end thereof, with the waste gas inlet opening, the fourth channel being formed, in an upper end thereof, with the waste gas outlet opening, the fourth channel being provided with the water blocking plates therein, the water blocking plates being provided in multiplicity.

5. The waste gas scrubbing tower according to claim 1, wherein the washing unit comprises a first washing assembly and a second washing assembly; the first washing assembly comprises a first pump assembly, a first water drawing pipe connected to the first pump assembly, a first water conveyance pipe assembly connected to the first pump assembly, a first pressure regulation pipe connected to the first pump assembly, and a plurality of first spraying head assemblies connected to the first water conveyance pipe assembly; and the second washing assembly comprises a second pump assembly, a second water drawing pipe connected to the second pump assembly, a second water conveyance pipe assembly connected to the second pump assembly, a second pressure regulation pipe connected to the second pump assembly, and a plurality of second spraying head assemblies connected to the second water conveyance pipe assembly.

6. The waste gas scrubbing tower according to claim 1, wherein the washing unit comprises a first washing assembly and a second washing assembly, the first washing assembly comprising a first pump assembly, a first water drawing pipe connected to the first pump assembly, a first water conveyance pipe assembly connected to the first pump assembly, a first pressure regulation pipe connected to the first pump assembly, and a plurality of first spraying head assemblies connected to the first water conveyance pipe assembly; the plurality of channels are, in sequence, a first channel, a second channel, a third channel, and a fourth channel; and the first spraying head assemblies are arranged in the first channel in a manner of being opposite to each other and position-shifted from each other in a vertical direction with some being arranged in the second channel.

7. The waste gas scrubbing tower according to claim 1, wherein the washing unit comprises a first washing assembly and a second washing assembly, the second washing assembly comprising a second pump assembly, a second water drawing pipe connected to the second pump assembly, a second water conveyance pipe assembly connected to the second pump assembly, a second pressure regulation pipe connected to the second pump assembly, and a plurality of second spraying head assemblies connected to the second water conveyance pipe assembly; the plurality of channels are, in sequence, a first channel, a second channel, a third channel, and a fourth channel; the second spraying head assemblies being arranged in the second channel and the third channel in a manner of being opposite to each other and position-shifted from each other in a vertical direction with some being arranged in the second channel in a manner of being position-shifted with respect to the first spraying head assemblies of the first washing assembly in the vertical direction, the second channel being additionally provided, on a top thereof, with the second spraying head assemblies.

8. The waste gas scrubbing tower according to claim 1, wherein the plurality of channels are, in sequence, a first channel, a second channel, a third channel, and a fourth channel; the filtration unit is mounted in the first channel, the second channel and the third channel and is arranged in the first channel, the second channel, and the third channel in a manner of being separated at upper and lower sides.

9. The waste gas scrubbing tower according to claim 6, wherein the first spraying head assemblies spray water jets in the form of water mist curtains that intersect and overlap each other.

10. The waste gas scrubbing tower according to claim 7, wherein the second spraying head assemblies spray water jets in the form of water mist curtains that intersect and overlap each other.

11. The waste gas scrubbing tower according to claim 2, wherein the plurality of channels of the tower body unit are connected to and in communication with each other, the plurality of channels being sequentially a first channel, a second channel, a third channel, and a fourth channel; the first channel is formed, in an upper end thereof, with the waste gas inlet opening, the fourth channel being formed, in an upper end thereof, with the waste gas outlet opening, the fourth channel being provided with the water blocking plates therein, the water blocking plates being provided in multiplicity.

* * * * *